United States Patent [19]

Kilham

[11] Patent Number: 5,191,388
[45] Date of Patent: Mar. 2, 1993

[54] APPARATUS FOR DETECTING AND ANALYZING PARTICULATE MATTER IN A SLURRY FLOW

[75] Inventor: Lawrence B. Kilham, Secaucus, N.J.

[73] Assignee: Flow Vision, Inc., Wilmington, Mass.

[21] Appl. No.: 809,348

[22] Filed: Dec. 18, 1991

[51] Int. Cl.$^5$ .................. G01N 21/00; G02B 6/04
[52] U.S. Cl. .................. 356/335; 356/338; 250/574; 250/227.28; 385/12
[58] Field of Search .................. 356/335–338, 356/339–343, 237–239, 73.1, 246, 440, 441, 436, 244; 250/574, 227.25, 227.28; 385/12, 43

[56] References Cited

U.S. PATENT DOCUMENTS

| 3,187,627 | 6/1965 | Kapany . | |
|---|---|---|---|
| 3,225,193 | 12/1965 | Hilton et al. | 250/227.28 |
| 3,819,278 | 6/1974 | Muller . | |
| 3,867,033 | 2/1975 | Hasinger | 250/227.28 |
| 3,975,084 | 8/1976 | Block | 356/244 |
| 4,385,830 | 5/1983 | Webb et al. | 356/338 |
| 4,432,642 | 2/1984 | Tulles | 356/246 |
| 4,529,306 | 7/1985 | Kilham et al. | 356/237 |
| 4,555,179 | 11/1985 | Langerholc et al. | 356/342 |
| 4,613,210 | 9/1986 | Pollard | 358/901 |
| 4,635,111 | 1/1987 | Moore | 358/106 |
| 4,661,845 | 4/1987 | Saito et al. | 356/246 |
| 4,664,513 | 5/1987 | Webb et al. | 356/338 |
| 4,672,437 | 6/1987 | Casper | 356/101 |
| 4,768,879 | 9/1988 | McLachlan et al. | 356/335 |
| 4,802,761 | 2/1989 | Bowen et al. | 356/246 |
| 4,804,268 | 2/1989 | Mohnsen et al. | 356/338 |
| 4,973,561 | 11/1990 | Hansen et al. | 356/436 |

Primary Examiner—Richard A. Rosenberger
Assistant Examiner—Hoa Q. Pham
Attorney, Agent, or Firm—Samuelson & Jacob

[57] ABSTRACT

Apparatus for detecting particulate matter in a slurry travelling in a flow channel, the apparatus including an optical taper containing a plurality of optical fibers fused together for viewing the particulate matter in only a thin layer of the slurry immediately adjacent to a first end of the optical fibers, the thin layer having a maximum depth equal to approximately the largest particle size of the particulate matter, the first ends of the optical fibers extending through a radial port in the flow channel and being immediately adjacent to the slurry travelling in the flow channel, the optical fibers having a focal length at the first ends thereof for permitting focussed viewing thereby only in the thin layer which is adjacent to the first ends, and the optical fibers being tapered from second opposite ends thereof to the first ends thereof to provide magnification of the image of the particulate matter at the second ends, a fiber optic bolt for securing the optical taper within the port such that the first ends of the optical fibers are in fluid communication with the slurry travelling in the flow channel, a light source for illuminating at least the thin layer of the slurry adjacent the first ends of the optical fibers, and a video camera for viewing an image of the particulate matter in the thin layer as viewed from opposite second ends of the optical fibers.

23 Claims, 3 Drawing Sheets

APPARATUS FOR DETECTING AND ANALYZING PARTICULATE MATTER IN A SLURRY FLOW

The present invention is related generally to apparatus for detecting and analyzing particulate matter in a slurry flow, and has particular applicability to manufacturing processes in the chemical, pulp and paper, food, beverage, mining, biological and pharmaceutical industries.

The presence of particulate matter in various slurries, such as those used in the paper making industry, will affect the quality of the finished products made from such slurries. For example, it may be important to determine the particle diameters of wood pulp in paper making slurries, since varying pulp fiber diameters, as well as bits of bark and ink globules, will not result in the production of acceptable paper.

However, various problems result with conventional apparatus used for detecting slurry particulate matter. In the first place, when viewing a slurry flow in a flow channel, there tends to be overlap or coincidence of neighboring particles from different depths within the flow channel. As a result, there is particle coincidence and it becomes difficult to obtain a usable image. In addition, because the particles are small, it has been necessary to provide magnification by using additional enlarging lenses, which further complicates the apparatus. Still further, it generally has been necessary to include at least two ports in the flow channel wall, each provided at an angle to the other, that is, one for illumination and one for viewing, as taught for example, in U.S. Pat. No. 4,529,306 having a common assignee herewith and the entire disclosure of which is incorporated herein by reference. Because two ports are required, the complexity of the mechanical arrangement is increased. It has also been known to use a single port which contains a laser illuminator and a separate photodetector. Such devices are sold by Laser Sensor Technology, Inc. of Bellevue, Wash.

Further, although various counters are known in the art for counting particles, these counters do not give a visual display so that it is difficult to determine whether the particulate matter consists of one particle or groups of particles, short or long pieces, the identity of the particulate matter such as fibrous material, bark, ink, dirt or the like, in pulp streams or, for example, jagged metal catalyst as distinguished from round plastic beads in some polymerization processes.

The present invention provides an apparatus which avoids many of the problems encountered in the above-outlined apparatus and exhibits several objects and advantages, some of which may be summarized as follows. First, because optical fibers have a small focal length, slurry particles viewed through optical fibers are viewed in only a first thin layer, typically 50 to 500 microns. Accordingly, there is little overlap or coincidence of neighboring particles. In addition, by tapering the optical fibers toward the ends of the optical fibers adjacent the slurry flow, the optical fibers themselves provide magnification without the need for additional lenses, although such lenses could be used to provide even greater enlargement and clarification. In addition, because the optical fibers are tapered into a tight bundle adjacent the slurry flow, the tapered ends provide a strong flat window for viewing the slurry, as a result of the great thickness and density of the bundle at the tapered end of the bundle. Still further, since only some of the optical fibers of the bundle are used for viewing, the remaining fibers can be used for illumination, or alternatively, the same optical fibers can be used for both illumination and observation. As a result, only one port or window in the flow channel wall is needed for viewing the slurry flow, thereby greatly simplifying the mechanical arrangement. With the present invention, it is also easy to observe the slurry flow by direct eye viewing, a video camera, a conventional photographic camera, a scanning or oscillating laser device, or with fiber optic imaging such as endoscopes or borescopes.

The above objects and advantages, as well as further objects and advantages, are attained by the present invention which may be described briefly as an apparatus for detecting particulate matter in a slurry travelling within a flow channel. The apparatus includes an optical transmission means for viewing the particulate matter in only a thin layer of the slurry immediately adjacent to the optical transmission means. In this regard, the optical transmission means has a focal length at a first end thereof immediately adjacent the thin layer of the slurry for permitting focussed viewing only in the thin layer. Preferably, the thin layer has a maximum depth equal to approximately the largest particle size of the particulate matter. The first end of the optical transmission means extends through a radial port in the flow channel so as to be positioned immediately adjacent the slurry travelling in the flow channel and, preferably, is positioned flush with an inner surface of the flow channel.

In one embodiment, the optical transmission means includes a flexible bundle of optical fibers. In another embodiment, the optical fibers are tapered from a smaller diameter first end adjacent the slurry, to a larger diameter second end to form an optical taper, which provides magnification of the image of the particulate matter at the first end, as viewed from the second end. In a third embodiment, the optical transmission means includes a rigid bundle of optical fibers of substantially uniform diameter which are fused together into a glass fiber image rod.

The optical transmission means is secured within the radial port in the flow channel by securing means such that the first end of the optical transmission means is immediately adjacent the slurry travelling in the flow channel. The securing means can take the form of a fiber optic bolt when the optical taper is used or a brass casing when the glass fiber image rod is used.

The invention further includes illuminating means for illuminating at least the thin layer of the slurry adjacent the first end of the optical transmission means. The illuminating means includes a light source, such as a laser diode, which projects light through some of the fibers in the optical taper, or through the optical fibers at the second end of the glass fiber image rod. In an alternative embodiment, the illuminating means can include a second fiber optic bundle which is oriented at an angle to the optical transmission means and which extends through a second radial port in the flow channel for illuminating the thin layer of the slurry.

Finally, the invention includes observation means for viewing an image of the particulate matter in the thin layer from the second end of the optical transmission means. Preferably, the observation means includes a video camera for receiving the image of the particulate matter in the thin layer from the second end of the optical transmission means and for producing a video signal in response thereto, and a video monitor for displaying the viewed image in response to the video signal from the video camera.

An image enhancement computer can be provided for electronically enhancing the image displayed by the monitor. In addition, an analysis computer can provide an analysis of particle size, type and quantity in the slurry in response to the video signal from the video camera.

The invention will be understood more fully, while still further objects and advantages will become apparent, in the following detailed description of preferred embodiments of the invention illustrated in the accompanying drawing, in which.

Figures 1, 2:
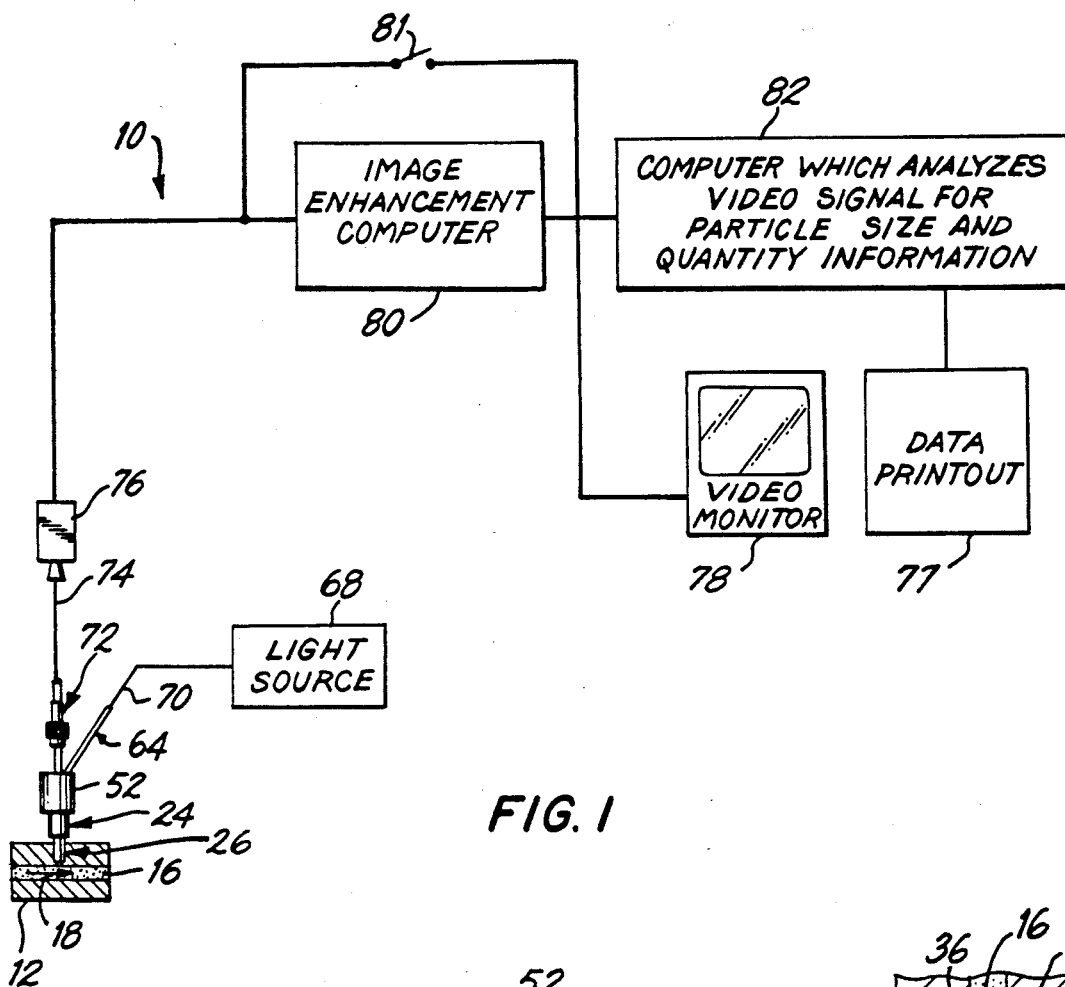
FIG. 1 is a schematic-block diagram of apparatus for detecting and analyzing particulate matter in a slurry flow according to one embodiment of the present invention.
FIG. 2 is an enlarged cross-sectional view of a portion of the apparatus of FIG. 1, showing illumination and viewing through the same fiber optic bundle.

Referring now to the drawing, and especially to FIGS. 1 and 2 thereof, an apparatus for detecting and analyzing particulate matter in a slurry flow, constructed in accordance with the present invention, is illustrated generally at 10. Apparatus 10 is shown in use with a walled flow channel 12 which carries a slurry 16 containing particulate matter 17, travelling in the direction of arrow 18.

The slurry can be of the type used, for example, in manufacturing processes in the chemical, pulp and paper, food, beverage, mining, biological and pharmaceutical industries, but is not limited to such processes. Generally, the particle sizes of the particulate matter are in the range of 5 to 2,000 microns, and more particularly, 20 to 500 microns, and still more particularly, in the range of 20 to 300 microns, with a typical size being approximately 50 to 200 microns. However, the size of the particulate matter will depend on the field of the particular manufacturing process. For example, in many chemical processes, filler additives contain finely ground hard compounds such as $TiO_2$ or carbon black, with particle sizes ranging from sub-micron to only a few microns. In such applications, a slurry particle analyzer constructed in accordance with the present invention can be used to determine the relative frequency of agglomerates of the finely ground particles, which agglomerates are typically 20 to 50 microns in size.

A particular applicability of the present invention is in the paper making industry. In such case, the industrial slurry will contain ink globules, dirt specks, fibrous material, extra large diameter pulp fibers conventionally termed "shives", pieces of plastic conventionally termed "stickies" and the like. Other common slurries are PVC powder in water, coal powder in water, adipic acid and the like. Generally, the solid content of the slurries will range from approximately 1% to 5% in the pulp and paper industry to approximately 10% to 35% in general chemical processes. Further, the slurries will be moving relatively fast in order to obtain a "plug flow" in which all particles move as a plug, that is, so that there is no gravimetric settling. Typically, the plug flow rate may be approximately one meter per second.

Figure 3:
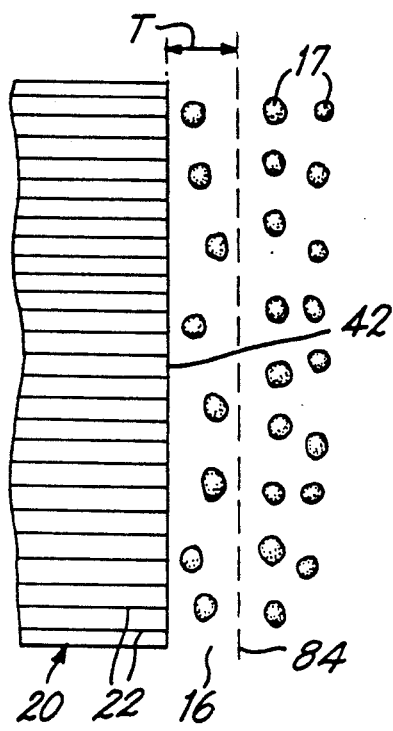
FIG. 3 is an enlarged schematic view of the tapered end of the fiber optic bundle being used to view only a first layer of the slurry flow adjacent the fiber optic bundle.

As shown best in FIGS. 2 and 3, apparatus 10 includes a fiber optic bundle 20 containing a plurality of optical fibers 22, each optical fiber 22 preferably having a diameter at the end thereof adjacent the slurry, in the range of approximately 20 to 70 microns. Optical fibers 22 are held together in a fiber optic bolt 24, and extend along the axial direction of fiber optic bolt 24 for substantially the entire length thereof. One end 26 of fiber optic bolt 24 is sealingly engaged within a radial port 28 in walled flow channel 12, which is in open communication with the interior of flow channel 12. End 26 of fiber optic bolt 24 can be sealingly engaged within radial port 28 by any suitable means. For example, as shown in FIG. 2, end 26 of fiber optic bolt 24 can have external threads 30 which threadedly engage with internal threads 32 of radial port 28. In addition, or as an alternative thereto, end 26 can be welded within port 28.

It is noted that fiber optic bolt 24 has a larger diameter middle section 34 extending through the exterior surface of walled flow channel 12 and a smaller diameter distal section 36 adjacent the inner wall of flow channel 12. Smaller diameter distal section 36 is connected with larger diameter middle section 34 and in axial alignment therewith. Therefore, an annular shoulder 38 is formed between larger diameter middle section 34 and smaller diameter distal section 36. This arrangement provides a two-fold purpose. First, by providing smaller diameter distal section 36, the intrusion through the inner surface of walled flow channel 12 is limited, and secondly, annular shoulder 38 provides a stop for fiber optic bolt 24 in order to accurately align the fiber optic bolt 24 within radial port 28. In this regard, fiber optic bolt 24 has a configuration corresponding to that of radial port 28.

With the configuration thus far described, it will be appreciated that one end face 42 of fiber optic bundle 20 is exposed to slurry 16 within flow channel 12 so as to view the slurry flow through flow channel 12. In this regard, the ends of optical fibers 22 are fused together at least at end face 42 of fiber optic bundle 20, and the circumference thereof can be frit welded to fiber optic bolt 24. The entire small diameter end face 42 is then ground and polished so as to provide a fused smooth surface which is substantially flush with the inner surface of walled flow channel 12. It will be appreciated that the grinding and polishing occurs while optical fibers 22 are positioned in fiber optic bolt 24 so that fiber optic bolt 24 is also polished at this end. Because optical fibers 22 are tapered into a tight bundle adjacent the slurry flow, the tapered ends provide a strong flat window for viewing the slurry. This is because of the great thickness and density of the bundle at the fused end face 42. For longer life and less abrasive deterioration from slurries, fiber bundle end face 42 can be protected by a thin diamond layer (not shown) achieved by a thin wafer adhered on fiber bundle end face 42 and having a thickness of 10 to 20 microns, or by vacuum deposition and having a thickness of several microns.

The opposite end 48 of fiber optic bolt 24 is mounted within a bore 50 of a housing 52. It will be appreciated that fiber optic bolt 24 also has a largest diameter proximal section 54 connected axially in line with larger diameter middle section 34 thereof. Largest diameter proximal section 54 is connected within housing 52.

As clearly shown in FIG. 2, the internal diameter of fiber optic bolt 24 increases from small diameter distal section 36 to larger diameter middle section 34 to largest diameter proximal section 54.

Figure 6:
FIG. 6 is a plan view of one tapered optical fiber for use with the fiber optic bundle or optical taper of the apparatus of FIG. 2.

In accordance with a preferred embodiment of the present invention, optical fibers 22 are fused together into an optical taper 56, and one end 58 of at least some optical fibers 22 have a smaller diameter than the opposite ends 60 thereof. Preferably, however, all optical fibers 22 in optical taper 56 have such a tapered configuration. Accordingly, these optical fibers 22 taper in diameter from ends 60 thereof which are positioned within housing 52, to ends 58 thereof which are positioned through radial port 28 of walled flow channel 12. One such optical fiber 22 is shown in FIG. 6. The amount of taper can vary, but will generally be in the range of three to six. As a result, each tapered optical fiber 22 will provide a magnification of the image, without the need for an enlargement lens. The magnification is determined by the diameter of the large diameter end 60 divided by the diameter of the small diameter end 58. This results in an effectively larger window to view slurry 16, while decreasing the size of radial port 28. In consequence thereof, apparatus 10 according to the present invention is more sensitive to detecting particulate matter in the slurry flow. Specifically, the particles can be read for a longer period of time at higher rates of speed for the slurry flow. The construction of an optical taper is conventional and is similar to that described in U.S. Pat. No, 3,187,627. In addition, Galileo Electro-Optics of Sturbridge, Mass. sells such optical tapers. Although the tapered optical fibers 22 provide an inherent magnification, it may be desirable to provide further magnification with an additional objective lens 62, as shown in FIG. 2, which is formed at the free end of observation probe 72. Such objective lens 62 is optional, and is not required with the present invention.

Typically, an optical taper 56 used with the present invention can have, for example, a small end diameter of ¼ inch, a large end diameter of 1 inch and a length of 3 to 4 inches.

Optical taper 56 is secured within fiber optic bolt 24 by any suitable means such as by epoxy at the transition between larger diameter middle section 34 and largest diameter proximal section 54. Alternatively, optical taper 56 can be removably secured within fiber optic bolt 24 so that optical tapers 56 having different magnifications can be used for different applications. For example, optical taper 56 can be threaded within fiber optic bolt 24.

Apparatus 10 further includes an illuminating probe 64 for illuminating at least some of the optical fibers 22 in fiber optic bundle 24. Illuminating probe 64 is conventional, and may be similar to the illuminating probe of commonly assigned U.S. Pat. No. 4,529,306. Thus, illuminating probe 64 extends through housing 52 such that the free end 66 thereof is positioned immediately behind some of the optical fibers 22 of optical taper 56. For example, free end 66 of illuminating probe 64 may be positioned behind peripherally arranged optical fibers 22 of optical taper 56, without providing illumination through centrally located ones of the optical fibers 22. Illuminating probe 64 is coupled to a light source 68 by means of a light-conducting guide 70, preferably in a form including a fiber optic bundle, which transmits light from light source 68 to illuminating probe 64. As a result, light supplied by illuminating probe 64 is carried by the respective optical fibers 22 to illuminate slurry 16 adjacent the small diameter ends of these optical fibers. Light source 68 can be any suitable light source, such as a laser diode, light emitting diode (LED) or other light source described in commonly assigned U.S. Pat. No. 4,529,306.

Figure 7:
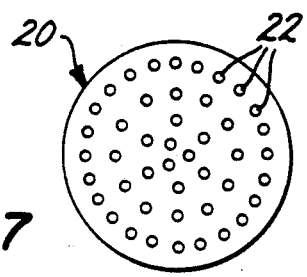
FIG. 7 is a plan view of the larger end of the optical taper of FIG. 2, showing individual optical fibers in the optical taper.

Apparatus 10 further includes an observation probe 72 for viewing particulate matter in the slurry flow through other tapered ones of the optical fibers 22 in optical taper 56. Preferably, as shown in FIGS. 2 and 7, centrally located optical fibers 22 are used for this purpose. It will be appreciated, however, that the same tapered optical fibers 22 can be used for both illumination and observation, if desired. Observation probe 72 can be constructed in the same manner as the observation probe described in commonly assigned U.S. Pat. No. 4,529,306, or can be of the type sold by Welch Allyn of Schenectady, N.Y. Observation probe 72 is coupled by cable 74 to a video camera 76 containing a conventional charge coupled device (CCD) or the like. Other recording means such as a data printout device 77, scanning or oscillating laser device, an endoscope or a borescope, can be used in place of video camera 76. It is important to note that focussing and imaging by any of these devices is easy and is not critical, because large ends 60 of optical fibers 22 present a relatively large image. Thus, high speed optical analysis can be used to determine relative particle sizes.

Video camera 76 converts the received optical image into electronic information which may be forwarded directly to a video monitor 78 which displays an image at a remote observation location for viewing by an observer to determine the size, density and the like of the particulate matter 17 in slurry 16. Optionally, an image enhancement computer 80, which can be the same as the image enhancement means of commonly assigned U.S. Pat. No. 4,529,306 may be utilized to enhance the image for increased accuracy and to aid in the analysis of the observed image. Image enhancement computer 80 can be connected in the circuit by closing a switch 81. As a further option, a computer 82 which analyzes the video signal for particle size and quantity information can be used. Such computer 82 is well known in, for example, the blood counting field, and uses conventional frame grab techniques.

It will be appreciated that illuminating probe 64 and observation probe 72 use the same optical taper 56 and, hence, the same radial port 28 through walled flow channel 12. This eliminates the need for providing a second radial port through walled flow channel 12, for example, as shown in U.S. Pat. No. 4,529,306.

In accordance with an important and essential aspect of the present invention, the focal length of optical fibers 22 which are used to view slurry 16 is very small such that only a thin layer 84 of slurry 16 is focussed for viewing, as shown best in FIG. 3. Such layer 84 preferably has a thickness T equal to the largest size of particulate matter 17 in slurry 16. As a result, overlap or coincidence of neighboring particles from different flow layers is avoided, so that a clearer image is obtained. In order to accomplish this result, the focal length of optical fibers 22 themselves are used, and there is no magnifying objective lens or the like positioned between ends 58 of optical fibers 22 and slurry 16. This is directly contrary to conventional fiber optical viewing apparatus, as shown, for example, in commonly assigned U.S. Pat. No. 4,529,306.

Thus, the present invention provides a focal length of optical fibers 22 that permits clear viewing of only a first layer 84 of particulate matter 17 in the rang of approximately 20 to 300 microns, and preferably 50 to 200 microns.

Generally, the distance that can be viewed which results in a clear image, that is, the maximum focal distance or length, is proportional to the reciprocal of the numerical aperture. As an example, the numerical aperture for the smaller end 58 of a focussed, tapered optical fiber 22 may be 1, providing a maximum focal distance of 125-300 microns, corresponding to the first layer 84 of slurry 16 adjacent thereto. In order to understand the numerical aperture in correspondence with the size of the particles, ground powder slurries generally have particle sizes of 100 to 200 microns. For comparison, the large end 60 of the same optical fiber 22 can have a numerical aperture of 0.3, which provides a maximum focal distance of 400-1,000 microns, and the end of fiber optic bundle 20 can have a numerical aperture of 0.6, which provides a maximum focal distance of 200-500 microns. The numerical aperture of an optical fiber is well defined, and represents the light-gathering capability of the fiber. See the article in Photonics Spectra, May, 1990, page 127 for a discussion of numerical apertures in relation to optical fibers.

Thus, because only the first thin layer 84 of particulate matter 17 adjacent optical fibers 22 is viewed, a clear and accurate image of the particulate matter is obtained. This image is further enhanced by the taper in optical fibers 22 which results in a magnification of 3 to 6 times the image obtained from ends 58 of optical fibers 22.

Figure 4:
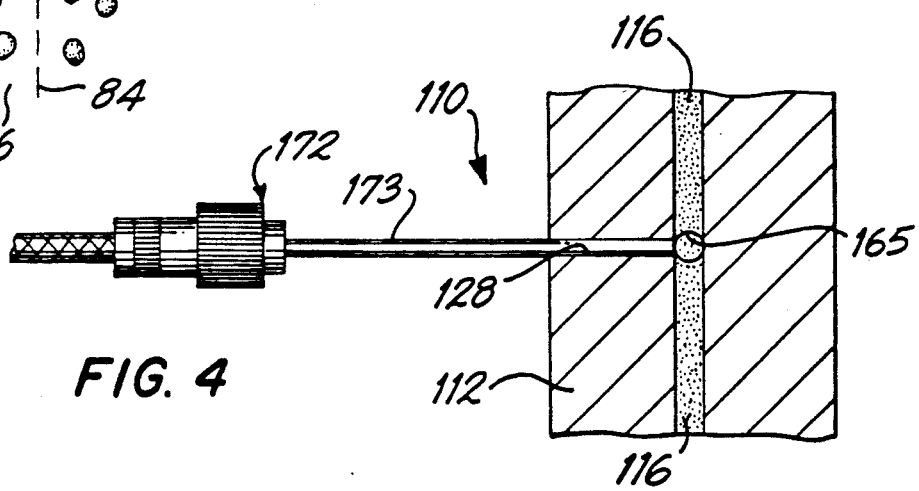
FIG. 4 is a partial cross-sectional view of a portion of apparatus for detecting and analyzing particulate matter in a slurry flow according to another embodiment of the present invention, in which an observation probe is oriented at an angle of approximately 90° to an illuminating probe.
Figure 5:
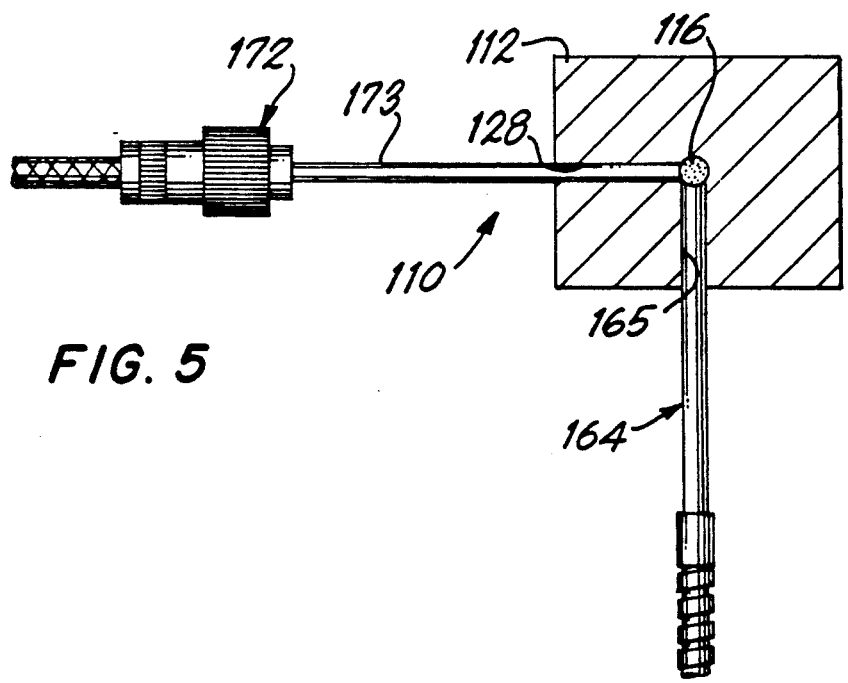
FIG. 5 is a partial cross-sectional view of the portion of the apparatus of FIG. 4, viewed from an angle 90° offset from the view of FIG. 4.

Referring now to FIGS. 4 and 5, an apparatus 110 for detecting and analyzing particulate matter in a slurry flow, constructed in accordance with another embodiment of the present invention, will now be described in which elements corresponding to those of apparatus 10 are identified by the same reference numerals augmented by 100, and a detailed description of such common elements will be omitted herein for the sake of brevity.

It will be appreciated that, while the tapered optical fibers 22 provide various advantages, the key to the present invention derives from viewing only the first layer 84 (FIG. 3) of particulate matter 17 in order to obtain high resolution of the particles. With apparatus 110, a non-tapered fiber optic bundle 173 is used. Accordingly, observation probe 172 itself is used to view a slurry 116, and there is no need to provide a fiber optic bolt or an optical taper, thereby simplifying the arrangement in comparison to apparatus 10. Observation probe 172 can be constructed in a similar manner to the observation probe of U.S. Pat. No. 4,529,306, the entire disclosure of which has been incorporated herein, with the following exceptions. Specifically, in observation probe 172, the fiber optic bundle 173 extends through radial port 128 and is positioned flush with the inner surface of walled flow channel 112. Thus, the observation window and objective lens of the observation probe of U.S. Pat. No. 4,529,306 are eliminated. Since the fiber optic bundle of observation probe 172 extends directly into contact with slurry 116, in the same manner as optical fibers 22 of apparatus 10, focussing occurs only with respect to the first layer of particulate matter. Of course, the fiber bundle end face can be protected by a thin diamond layer as discussed above with respect to the first embodiment.

In addition, illuminating probe 164 is positioned through another radial port 165 in walled flow channel 112 at an angle with respect to observation probe 172. Although the angle shown in FIGS. 4 and 5 is 90°, this angle can be varied. Even though illuminating probe 164 illuminates the entire area therearound, including the area viewed by observation probe 172, observation probe 172 still only focusses on the first layer of particulate matter. The angle between illuminating probe 164 and observation probe 172 will be determined by the particles to be viewed, in the manner taught by commonly assigned U.S. Pat. No. 4,529,306, and in particular, will depend on the transparency or opacity of the particles.

Figure 8:
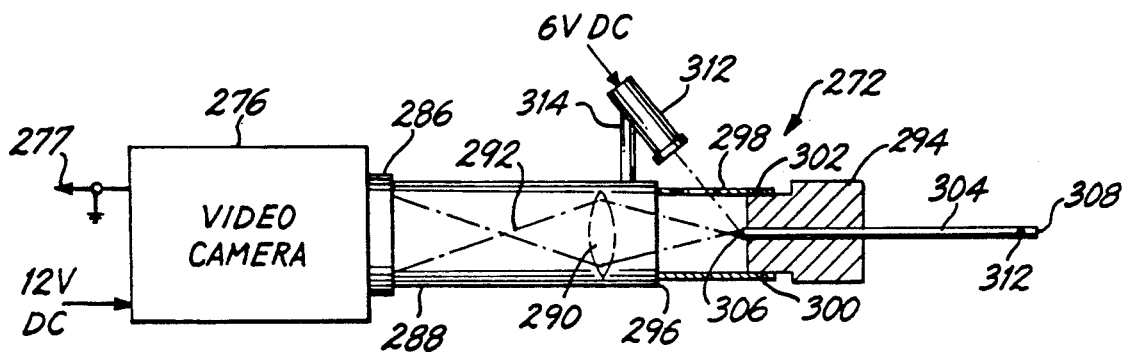
FIG. 8 is a schematic elevational view, partly in phantom, of apparatus for detecting and analyzing particulate matter in a slurry flow according to still another embodiment of the present invention.
Figures 9, 10:
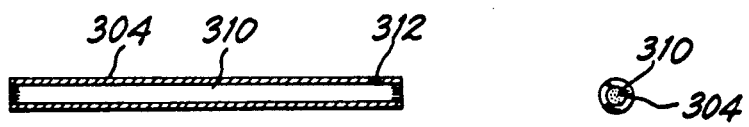
FIG. 9 is a cross-sectional view of the observation probe of the apparatus of FIG. 8.
FIG. 10 is an end plan view of the observation probe of FIG. 9.

Referring now to FIGS. 8 through 10, a specific construction of an observation probe 272 and video camera 276 according to another embodiment of the invention is shown, in which elements corresponding to those of observation probe 172 and camera 176 are identified by the same reference numerals augmented by 100. This construction has particular applicability for paper pulp slurries. Specifically, a conventional CCD video camera 276 is connected to a black and white RS-170 video output line 277. The opposite input end of video camera 276 is connected by a C-mount coupling 286 to an aluminum relay lens enclosure 288 that contains a relay lens 290 mounted therein. Relay lens 290 supplies and enlarges the signal from the proximal end of the fiber optic bundle to the input lens of video camera 276, via the path shown by dashed lines 292.

The opposite end of relay lens enclosure 288 is coupled to a solid brass nose piece 294 through a C-mount coupling 296 and a brass interconnector 298, the latter being connected with nose piece 294 by fine threads 300. As a result, the position of nose piece 294 with respect to relay lens 290 can be adjusted. The position of nose piece 294 can be removably fixed by means of a set screw 302 extending through brass interconnector 298 and nose piece 302.

A brass casing 304 is fixedly connected to nose piece 294 along a central axial line thereof. Brass casing 304 has a proximal end 306 extending rearwardly of nose piece 294 and an opposite distal end 308 extending forwardly of nose piece 294. Brass casing 304 surrounds and supports a glass fiber image rod 310 which is seating in the casing and secured therein by a set screw 312. Glass fiber image rod 310 is formed by a rigid bundle of optical fibers of substantially uniform diameter which are fused together. In addition, although not shown, a PVC tubular intermediate layer may be provided between glass fiber image rod 310 and brass casing 304. Brass casing 304 is mounted within a radial port of a walled flow channel in order to view the particulate matter within a slurry, and transmits a coherent image to video camera 276 through relay lens 290. Glass fiber image rod 310 can, for example, have a diameter of ⅛ inch and a length of 1 to 6 inches.

In order to provide illumination, a 3 MW red laser diode 314 is mounted to relay lens enclosure 292 by a mechanical mount 316 and is aimed at the proximal end of glass fiber image rod 310. Accordingly, both illumination and observation occur through optical fibers of glass fiber image rod 310.

It is to be understood that the above detailed description of preferred embodiments of the invention are provided by way of example only. Various details of design, construction and procedure may be modified without departing from the true spirit and scope of the invention as set forth in the appended claims.

The embodiments of the invention in which an exclusive property or privilege is claimed are defined as follows:

1. Apparatus for detecting particulate matter in a slurry travelling in a flow channel, said apparatus comprising:
   optical transmission means for viewing the particulate matter in only a thin layer of said slurry adjacent to said optical transmission means, said thin layer having a maximum depth equal to approximately the largest particle size of said particulate matter, said optical transmission means including a first end and an opposite second end, said first end extending through a port in said flow channel and being adjacent the slurry travelling in the flow channel, and said optical transmission means having a focal length at said first end for permitting focussed viewing by said optical transmission means only in said thin layer which is adjacent to said first end;
   securing means for securing said optical transmission means within said port such that said first end of said optical transmission means is adjacent the slurry travelling in the flow channel;
   illuminating means for illuminating at least said thin layer of said slurry adjacent said first end of said optical transmission means; and
   observation means for viewing an image of said particulate matter in said thin layer from the second end of said optical transmission means.

2. Apparatus according to claim 1, wherein said optical transmission means includes at least one optical fiber.

3. Apparatus according to claim 2, wherein said optical transmission means includes a bundle of optical fibers.

4. Apparatus according to claim 3, wherein said bundle of optical fibers are fused together.

5. Apparatus according to claim 3, wherein a plurality of said optical fibers are tapered from said second end to said first end, and said observation means is positioned adjacent the tapered optical fibers at said second end, such that said tapered optical fibers provide a magnification of the image of the particulate matter at said first end.

6. Apparatus according to claim 5, wherein substantially all of said optical fibers are tapered and are fused together into an optical taper.

7. Apparatus according to claim 3, wherein said illuminating means is positioned adjacent a first set of optical fibers of said bundle at said second end for projecting light therethrough to said first end in order to illuminate said thin layer immediately adjacent said first end, and said observation means is positioned adjacent a different second set of optical fibers of said bundle at said second end for receiving an image therefrom.

8. Apparatus according to claim 3, wherein said illuminating means is positioned adjacent a first set of optical fibers of said bundle at said second end for projecting light through said first set to said first end in order to illuminate said thin layer immediately adjacent said first end, and said observation means is also positioned adjacent the first set of optical fibers of said bundle at said second end for receiving an image from said first set.

9. Apparatus according to claim 1, wherein said optical transmission means includes a glass fiber image rod of substantially uniform diameter.

10. Apparatus according to claim 9, wherein said illuminating means is positioned adjacent the glass fiber image rod at said second end for projecting light through the rod to said first end in order to illuminate said thin layer immediately adjacent said first end, and said observation means is also positioned adjacent the glass fiber image rod at said second end for receiving an image from the rod.

11. Apparatus according to claim 1, wherein said first end is in fluid communication with the slurry.

12. Apparatus according to claim 1, further including lens means for magnifying an image received from the second end of the optical transmission means and for supplying the magnified image to the observation means.

13. Apparatus according to claim 1, wherein said flow channel has an inner wall, and said first end is flush with the inner wall of said flow channel.

14. Apparatus according to claim 1, wherein said securing means includes bolt means for holding said optical transmission means therein, said bolt means being secured within said port.

15. Apparatus according to claim 1, wherein said securing means includes casing means for holding said optical transmission means therein, said casing means being secured within said port.

16. Apparatus according to claim 1, wherein said flow channel includes a second port offset from the first-mentioned port in the flow channel, and said illuminating means is positioned in said second port.

17. Apparatus according to claim 16, wherein said illuminating means includes second optical transmission means having a first end and a second end, the first end extending through the second port of said flow channel and being adjacent the slurry, and light source means for supplying light to said second end of said optical transmission means.

18. Apparatus according to claim 17, wherein said light source means includes a laser diode.

19. Apparatus according to claim 1, wherein said illuminating means includes a laser diode.

20. Apparatus according to claim 1, wherein said observation means includes video camera means for receiving the image of said particulate matter in said thin layer from the second end of said optical transmission means and for producing a video signal in response thereto, and monitor means for displaying the viewed image in response to the video signal from said video camera means.

21. Apparatus according to claim 20, further including image enhancement means for electronically enhancing the image displayed by said monitor means.

22. Apparatus according to claim 20, further including analysis means for providing an analysis of particle size in response to the video signal from the video camera means.

23. Apparatus according to claim 20, further including analysis means for providing an analysis of the quantity of particulate matter in the slurry in response to the video signal from the video camera means.

* * * * *